(12) United States Patent
Zhang

(10) Patent No.: US 8,744,549 B2
(45) Date of Patent: *Jun. 3, 2014

(54) SUBDERMAL NEEDLE ELECTRODE CABLE ASSEMBLY HAVING MOVABLE NEEDLE SAFETY COVER INTEGRAL THEREWITH

(71) Applicant: Xialing Zhang, Mountain View, CA (US)

(72) Inventor: Xialing Zhang, Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/851,172

(22) Filed: Mar. 27, 2013

(65) Prior Publication Data
US 2013/0211225 A1   Aug. 15, 2013

Related U.S. Application Data

(63) Continuation of application No. 12/925,861, filed on Nov. 1, 2010, now Pat. No. 8,433,386.

(60) Provisional application No. 61/280,326, filed on Nov. 2, 2009.

(51) Int. Cl.
*A61B 5/0492* (2006.01)
*A61N 1/05* (2006.01)

(52) U.S. Cl.
USPC ............................... 600/373; 607/116

(58) Field of Classification Search
CPC . A61B 5/04001; A61B 5/0492; A61B 5/6848
USPC .......................................... 600/373; 607/116
See application file for complete search history.

(56) References Cited

U.S. PATENT DOCUMENTS

| | | | |
|---|---|---|---|
| 6,539,264 B1* | 3/2003 | Bishay et al. | 607/46 |
| 6,912,424 B2* | 6/2005 | Bishay et al. | 607/46 |
| 8,433,386 B2* | 4/2013 | Zhang | 600/373 |
| 2004/0172115 A1* | 9/2004 | Miazga et al. | 607/116 |
| 2009/0036765 A1* | 2/2009 | Espenhain | 600/373 |
| 2010/0234713 A1* | 9/2010 | Sheraton, Sr. | 600/373 |

* cited by examiner

*Primary Examiner* — Lee S Cohen
(74) *Attorney, Agent, or Firm* — David O. Simmons

(57) ABSTRACT

A cable assembly comprising a signal conductor, a needle electrode electrically connected to the signal conductor and a safety cover having a central passage therein. The signal conductor extends through the central passage. The safety cover is moveable along the signal conductor for allowing the needle electrode to become positioned within the central passage.

20 Claims, 2 Drawing Sheets

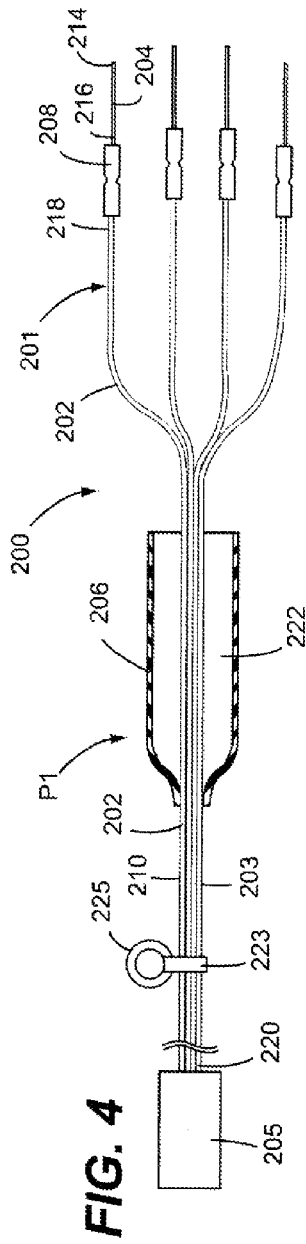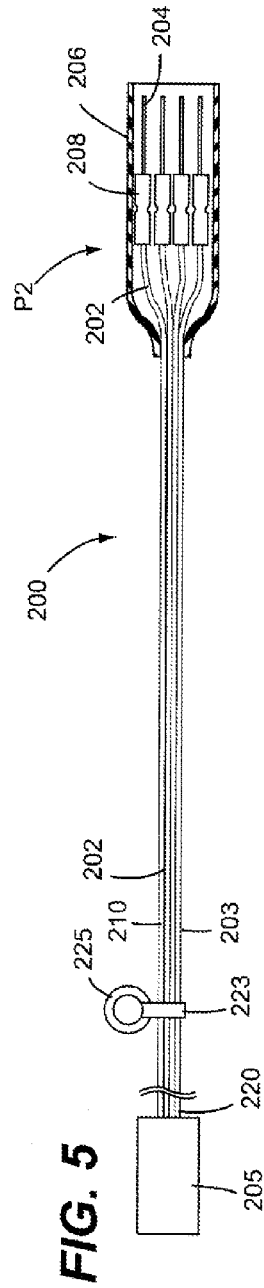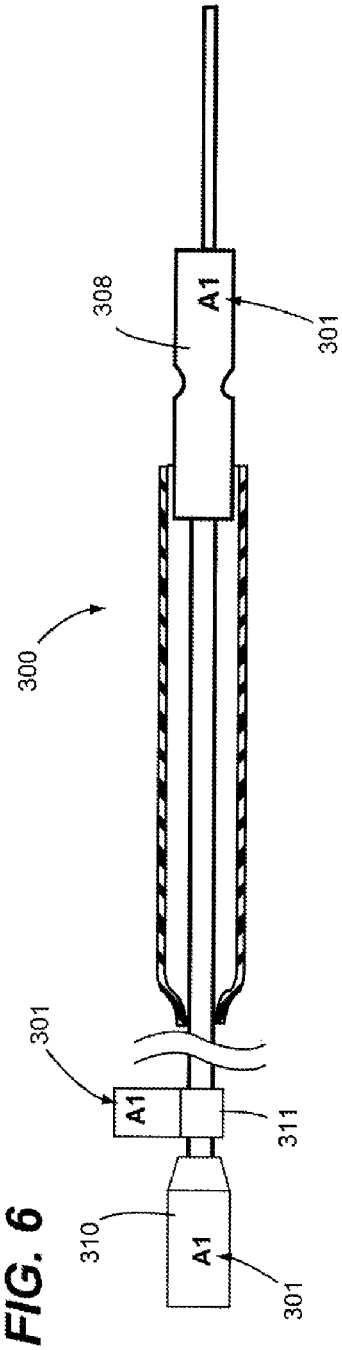

SUBDERMAL NEEDLE ELECTRODE CABLE ASSEMBLY HAVING MOVABLE NEEDLE SAFETY COVER INTEGRAL THEREWITH

CROSS REFERENCE TO RELATED APPLICATIONS

This continuation patent application claims priority from U.S. Non-provisional patent application having Ser. No. 12/925,861 filed Nov. 1, 2010 entitled "Subdermal needle electrode cable assembly having movable needle safety cover integral therewith", now U.S. Pat. No. 8,433,386 issued on 30-Apr. 2013, which claims priority from U.S. Provisional Patent Application having Ser. No. 61/280,326 filed Nov. 2, 2009 entitled "Subdermal Electrode Safety Cover And Pre-assembled Multi-Paired Electrodes With Wire String And Bundle Holder", both of which have a common applicant and inventor herewith and are both being incorporated herein in their entirety by reference.

FIELD OF THE DISCLOSURE

The disclosures made herein relate generally to subdermal needle electrodes and, more particularly, to subdermal needle electrode cable assemblies having a protective implement integral therewith for selectively concealing the subdermal needle electrode thereof.

BACKGROUND

Currently available subdermal needle electrodes (i.e., conventional subdermal needle electrodes) are typically provided in the form of an assembly consisting of a metal needle electrode (stainless steel, platinum, tungsten etc.), lead wire, connector fixedly joining the metal needle electrode to a first end portion of the lead wire, and an electrical plug connected to a second end portion of the lead wire. This assembly is referred to herein as a subdermal needle electrode cable assembly, which is typically offered as a single subdermal needle electrode cable assembly in a sterile-packaged or a set (e.g., pair) of subdermal needle electrode cable assemblies in a sterile package.

Subdermal needle electrodes are used in neurological and neurophysiological studies for recording a variety of types of neurological and neurophysiological signals. Examples of such signals include, but are not limited to, electroencephalogram (EEG) signals, spontaneous or triggered electromyogram (EMG) signals, somatosensory evoked potential (SSEP) signals, transcranial motor evoked potential (tcMEP) signals, brainstem auditory evoked potential (BAER) signals, and visual evoked potential (VEP) signals. The studies generally occur in various environments such as, for example, a hospital intensive care unit (ICU), an in-patient setting (e.g., clinic), and in an operating room (e.g., at a hospital). Intraoperative neuromonitoring (IOM) is a common type of intraoperative neurophysiological study and can include any combination of EEG, SSEP, tcMEP, EMG, BAER, or VEP signal monitoring during neurosurgery, orthopedic surgery, cardiovascular surgery and neurovascular surgery. During such types of surgeries, neural structures are often at risk for loss of function and, thus, the benefit of monitoring such function with IOM.

Intraoperative neuromonitoring has developed rapidly over the last several years. Furthermore, it has become a standard aspect of care in the modern surgical procedures outlined above. Intraoperative neuromonitoring is required in a considerable number of surgical procedures every day in US and many other countries around the world. Most of the procedures require 20-40 subdermal needle electrodes. Thus, a very large number of subdermal needle electrodes are used daily throughout the United States as well as many other countries around the world.

In one example, subdermal needle electrodes are applied through the skin to reach the target muscle groups for EMG recording and subcutaneously in the scalp for SSEP recording. Optionally, electrodes can also be applied subcutaneously in the scalp for transcranial motor stimulation. Intraoperative neuromonitoring is an extremely important tool for providing the surgeon with constant functional assessment of the central and peripheral nervous systems. Subdermal electrode needles are not reusable and, thus, require disposal after use. Because subdermal needle electrodes need to penetrate the skin in the patients, they must be considered to carry bloodborne pathogens after use.

Currently available FDA-approved subdermal needle electrodes have a protective cover over the needle to keep the needle sterile in its package and prior to use as well as prevent needle sticks prior to its use. However, they do not have any safety features to prevent or limit the potential for needle sticks once they are removed from a patient. With the considerable number of intraoperative neuromonitoring procedures in the US and worldwide, needle stick incidents from subdermal needle electrodes by healthcare professional and surgeons are not uncommon.

To handle a total of 20-40 single electrodes or paired electrodes in a time-critical operating room, a high rate of needle stick incidents occur to neurophysiologists, neuromonitoring technicians, nurses, anesthesiologist, surgeons and room helpers. This type of surgery requires teamwork with many surgical staff members working simultaneously on the patient especially at the beginning and end of surgery. The needle electrodes must be removed from the patient before recovery from the anesthesia. This is an extremely hazardous procedure when 20-40 single or 10-20 pairs of subdermal needle electrodes are individually removed from the patient's body. The removed needle electrodes are open and exposed until their final collection and disposal. During this time, all of the surgical staff are at risk of a needle stick, which could potentially transmit hazardous bloodborne pathogens and/or infectious diseases. Examples of such hazardous bloodborne pathogens and/or infectious diseases include, but are not limited to, Human Immunodeficiency Virus (HIV), Hepatitis B, Hepatitis C and Creutzfeldt-Jakob Disease (CJD).

In October of 2000, "The Needlestick Safety and Prevention Act" (i.e., the ACT) was passed in the United States Senate (October 3$^{rd}$) and United States House of Representatives of The United States of America (October 26$^{th}$) in United States Congress. In response to this law, the US Department of Labor revised "The Bloodborne Pathogens Standard" in January of 2001. The Act presents various aspects of the requirement for use of engineering and work practice controls to eliminate or minimize employee exposure to bloodborne pathogens. The Act presents information relating to changes in technology that eliminate or reduce exposure to bloodborne pathogens. The Act states that numerous studies have demonstrated that the use of safer medical devices, such as needleless systems and sharps with engineered sharps injury protections, when they are part of an overall bloodborne pathogens risk-reduction program, can be extremely effective in reducing accidental sharps injuries. The Act also states that, in March of 2000, the Centers for Disease Control and Prevention estimated that 62 to 88 percent of sharps injuries could potentially be prevented by the use of safer medical devices.

The traditional design of the subdermal needle electrode has existed for many years without change. More specifically, no currently-available FDA-approved subdermal needle electrode have any type of safety device that prevents or substantially limits the potential for sticks by the needle electrode after it has been removed from a patient. Therefore, a subdermal needle electrode cable assembly that overcomes drawbacks associated with currently available subdermal needle electrode cable assemblies not preventing or substantially limits the potential for needle sticks would be advantageous, desirable and useful.

SUMMARY OF THE DISCLOSURE

Embodiments of the present invention relate to subdermal needle electrodes that are used in neurological and neurophysiological studies. Such subdermal needle electrodes include one or more features that contribute to a safer and/or more efficient work environment for health care providers involved in the installation, use, and removal of subdermal needle electrodes. Advantageously, these features, individually and in combination, aid in reducing needle stick incidents, which frequently occur in health care settings where subdermal needle electrodes are used. One example of such a feature is a needle safety cover configured to prevent or limit the potential for needle sticks after the subdermal needle electrode is removed from a patient. Another example of such a feature is identifying information (e.g., numeric indicia and/or color-coding) to assist in identifying a particular one of a plurality of subdermal needle electrodes that are being used for a patient. Another example of such a feature is a distinctive visual appearance that adds a visual safety warning of the needle electrode when it is implanted and subsequently removed for collection and disposal. Still another example of such a feature is a cable unit including a plurality of interconnected subdermal needle electrode cable assemblies. Yet another example of such a feature is a cable retention structure integral with the lead wires (i.e., signal conductors) of subdermal needle electrode cable assemblies. Thus, a skilled person will appreciate that a subdermal needle electrode cable assembly configured in accordance with the present invention advantageously overcomes one or more shortcomings associated with conventional subdermal needle electrode cable assemblies.

In one embodiment of the present invention, an apparatus for monitoring neurological and/or neurophysiological signals of a patient comprises a signal conductor, an electrode, and a safety cover. The signal conductor has a first end portion and a second end portion. The electrode has a first end portion and a second end portion. The first end portion is a skin piercing portion of the electrode and the second end portion is electrically connected to the first end portion of the signal conductor. The safety cover has an electrode shrouding space therein. The electrode shrouding space is configured in a manner allowing the first end portion of the electrode to be positioned within the electrode shrouding space as a result of the safety cover being moved along a length of the signal conductor toward the first end portion of the electrode.

In another embodiment of the present invention, a subdermal needle electrode cable assembly comprises a needle electrode, a lead wire, a first electrical connector, and a safety cover. The needle electrode has a first end portion and a second end portion. The first end portion of the needle electrode is configured for piercing skin of a patient. The lead wire has a first end portion and a second end portion. The first electrical connector is electrically connected to the second end portion of the needle electrode and the first end portion of the lead wire for providing electrical continuity between the needle electrode and the lead wire. The safety cover is moveable mounted on the lead wire. The lead wire extends through a central passage of the safety cover. The safety cover is movable between a position in which at least the first end portion of the needle electrode is exposed outside of the central passage and a position in which an entire portion of the needle electrode becomes positioned within the central passage.

In another embodiment of the present invention, a cable unit including a plurality of subdermal needle electrodes cable assemblies comprises a cable, a plurality of needle electrodes, and a safety cover. The cable has a plurality of signal conductors each having a first end portion and a second end portion. The plurality of needle electrodes each has a first end portion and a second end portion. The first end portion of each one of the needle electrodes is configured for piercing skin of a patient and the second end portion of each one of the needle electrodes is electrically connected to the first end portion of a respective one of the signal conductors. The safety cover is moveably mounted on the cable. The cable extends through a passage within the safety cover. The safety cover is movable with respect to the cable between a position in which an entire portion of each one of the needle electrodes is exposed outside of the passage and a position in which the entire portion of each one of the needle electrodes becomes positioned within the passage.

These and other objects, embodiments, advantages and/or distinctions of the present invention will become readily apparent upon further review of the following specification, associated drawings and appended claims.

BRIEF DESCRIPTION OF THE DRAWINGS

The present invention will be described with reference to the attached drawings which are given as non-limiting examples only, in which:

FIG. 4 is a partial cross-sectional view showing a subdermal needle electrode cable unit configured in accordance with an embodiment of the present invention, wherein a safety cover is in its initial position with respect to needle electrodes of the cable unit;

FIG. 5 is a partial cross-sectional view of the subdermal needle electrode cable unit shown in FIG. 4, wherein the safety cover is in a needle electrode concealing position; and FIG. 6 is a partial cross-sectional view showing a subdermal needle electrode cable assembly having integral therewith identifying information configured in accordance with an embodiment of the present invention.

DETAILED DESCRIPTION OF THE DRAWING FIGURES

Figure 1:
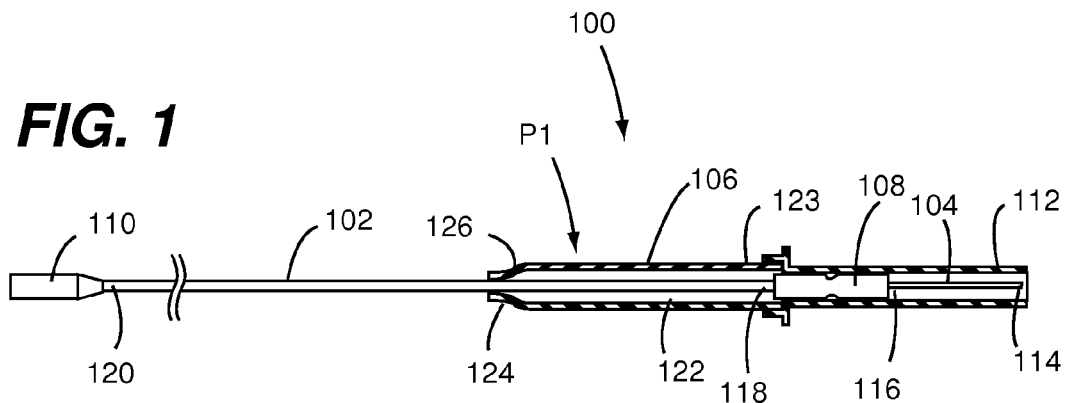
FIG. 1 is a partial cross-sectional view showing a subdermal needle electrode cable assembly configured in accordance with an embodiment of the present invention, wherein a safety cover and protective cover are each in their initial positions with respect to a needle electrode of the subdermal needle electrode cable assembly.
Figure 2:
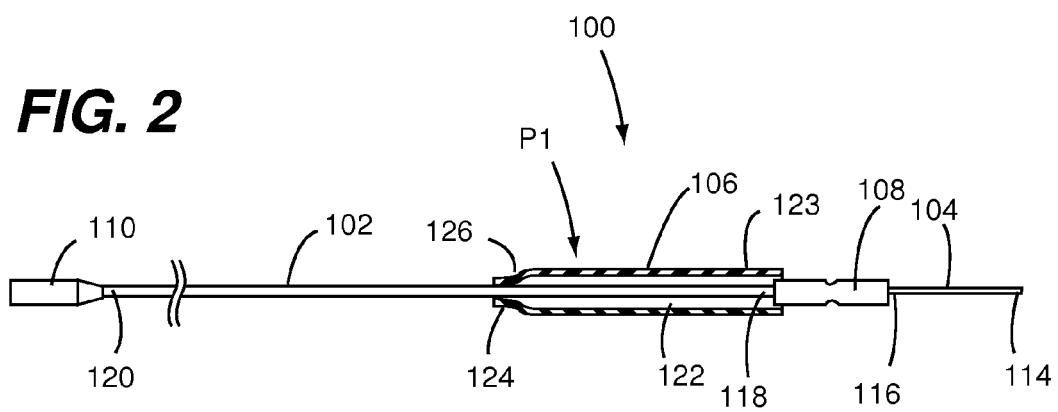
FIG. 2 is a partial cross-sectional view of the subdermal needle electrode cable assembly shown in FIG. 1, wherein the protective cover is removed.
Figure 3:
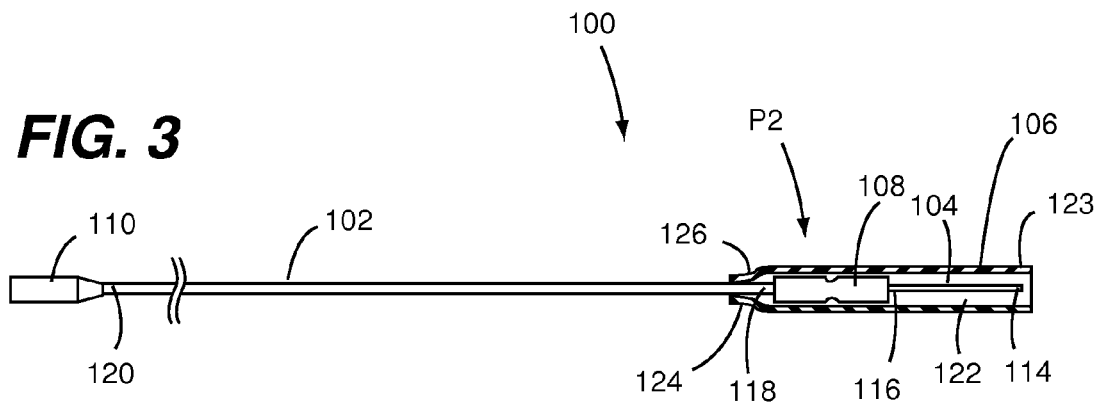
FIG. 3 is a partial cross-sectional view of the subdermal needle electrode cable assembly shown in FIG. 1, wherein the safety cover is in a needle concealing position.

FIGS. 1-3 show a subdermal needle electrode cable assembly 100 configured in accordance with an embodiment of the present invention. The subdermal needle electrode cable assembly 100 is an example of an apparatus configured in accordance with the present invention for monitoring neurological and/or neurophysiological signals of a patient. Examples of such signals include, but are not limited to, electroencephalogram (EEG) signals, spontaneous or triggered electromyogram (EMG) signals, somatosensory evoked potential (SSEP) signals, transcranial motor evoked potential (tcMEP) signals, brainstem auditory evoked potential (BAER) signals, and visual evoked potential (VEP) signals.

The subdermal needle electrode cable assembly 100 includes a lead wire 102, a needle electrode 104, a safety cover 106, a first electrical connector 108, a second electrical connector 110, and a protective cover 112. The needle electrode 104 has a first end portion 114 and a second end portion 116. The first end portion 114 of the needle electrode 104 is configured for piercing skin of a patient. For example, the first end portion 114 of the needle electrode 104 can be sharpened. Straight needle electrodes and hook needle electrodes are two known types of needle electrodes. The lead wire 102 has a first end portion 118 and a second end portion 120. The first electrical connector 108 is electrically connected to the second end portion 116 of the needle electrode 104 and the first end portion 118 of the lead wire for providing electrical continuity between the needle electrode 104 and the lead wire 102. The second electrical connector 110 is connected to the second end portion 120 of the lead wire 102 for allowing the subdermal needle electrode cable assembly 100 to be electrically connected to signal monitoring equipment used in monitoring neurological and/or neurophysiological signals. In general, a typical procedure in which monitoring of neurological and/or neurophysiological signals of a patient is performed will require a plurality of subdermal needle electrode cable assemblies to be connected between the patient and the signal monitoring equipment.

It is disclosed herein that the first electrical connector 108 and the second electrical connector 110 can each include an electrically insulating cover and an electrically conductive element with the electrically insulating cover. Similarly, the lead wire can include an electrically insulating cover with an electrically conductive core extending the length of the electrically insulating cover (i.e., an insulated single strand or multi-strand wire). In the case of the first electrical connector 108, the electrically conductive element is electrically connected to both the needle electrode 104 and to the electrically conductive core of the lead wire 102 (e.g., by means such as crimping, mechanical interference, soldering, ultrasonic welding, or the like). In the case of the second electrical connector 110, the electrically conductive element is electrically connected to the electrically conductive core of the lead wire 102 and is configured for being disengagably engaged with a signal receiving terminal or port of the signal monitoring equipment.

Preferably, but not necessarily, an exterior surface of the first electrical connector 108 is brightly colored (e.g., bright orange, florescent green, etc) and/or has an otherwise very distinctive visual appearance (e.g., multi-color pattern). Such distinctive visual appearance adds a visual safety warning of the needle electrode 104 when it is implanted and subsequently removed for collection and disposal. In this manner, subdermal needle electrode cable assemblies configured in accordance with the present invention can be configured for enhancing attention to the needle electrodes thereby reducing the potential for needle stick incidents.

The safety cover 106 is slideably (i.e., moveable) mounted on the lead wire 102. The lead wire 102 extends through a central passage 122 of the safety cover 106. The safety cover is movable between a first position P1 (FIG. 1) in which at least the first end portion 114 of the needle electrode 104 is exposed outside of the central passage 122 and a second position P2 (FIG. 3) in which an entire portion of the needle electrode 104 becomes positioned within the central passage 122. In this manner, the central passage 122 is sized and/or otherwise configured to receive the first connector 108 and the needle electrode 104 therein, thereby providing a needle electrode shrouding space that extends through a first end portion 123 of the safety cover 106.

The central passage 122 includes a reduced cross sectional portion 124 at a second end portion 126 of the safety cover 106. The reduced cross sectional portion 124 causes the safety cover 106 to engage the first electrical connector 108 for defining a maximum amount of displacement of the safety cover 106 with respect to the needle electrode 104 when the safety cover 106 is being moved toward the first end portion 114 of the needle electrode 104. The reduced cross sectional portion 124 is one example of a means for defining a maximum amount of displacement of the safety cover 106 with respect to the needle electrode 104. It is disclosed herein that other such means can be implemented in place of or in conjunction with the reduced cross sectional portion 124. Examples of such means include, but are not limited to, one or more protrusions within the central passage 122, an end cap with a hole therein attached to the second end portion 126 of the safety cover 106, and the like.

It is disclosed herein that the safety cover 106 can be configured for limiting or precluding unintentional movement toward the first position P1 once it is in the second position P2 (i.e., an entire portion of the needle electrode 104 becomes positioned within the central passage 122). In one embodiment, the reduced cross sectional portion 124 of the central passage 122 and the lead wire 102 are jointly configured whereby friction therebetween provides for limiting or precluding unintentional movement of the safety cover 106 toward the first position P1 once it is in the second position P2. In another embodiment, the central passage 122 and the first electrical connector 108 are jointly configured to limit or preclude unintentional movement of the safety cover 106 toward the first position P1 once it is in the second position P2. For example, the central passage 122 and the first electrical connector 108 can be jointly configured whereby friction therebetween limits or precludes unintentional movement of the safety cover 106 toward the first position P1 once it is in the second position P2, the central passage 122 and/or the first electrical connector 108 can include a mechanical interlock structure that limits or precludes unintentional movement of the safety cover 106 toward the first position P1 once it is in the second position P2, etc. It is disclosed herein that the present invention is not unnecessarily limited to any particular means for limiting or precluding unintentional movement of the safety cover 106 toward the first position P1 once it is in the second position P2. For example, the resiliency/flexibility of the lead wire 102 can be sufficient to limit or preclude unintentional movement of the safety cover 106 toward the first position P1 once it is in the second position P2.

The protective cover 112 is removably secured over the first end portion 114 of the needle electrode 104 for concealing the first end portion 114 of the needle electrode 104 prior to its use. The safety cover 106 is inhibited from being moved along the length of the lead wire 102 toward the first end portion 114 of the needle electrode 104 for causing the first end portion 114 of the needle electrode 104 to become positioned within the central passage 122 of the safety cover 106 until the protective cover 112 is removed from its secured position over the first end portion 114 of the needle electrode 104.

Referring now to FIGS. 4 and 5, a cable unit 200 configured in accordance with an embodiment of the present invention is shown (i.e., a subdermal needle electrode cable unit). The cable unit 200 bundles (i.e., unitizes) a plurality of subdermal needle electrodes cable assemblies 201 such that it is not necessary to individually handle the plurality of subdermal needle electrodes cable assemblies 201. Furthermore, the cable unit 200 can be configured for allowing the plurality of subdermal needle electrodes cable assemblies 201 to be simultaneously connected to signal monitoring equipment. To this end, in one embodiment, each one of the subdermal needle electrodes cable assemblies 201 can be constructed essentially the same as the subdermal needle electrodes cable assembly 100 of FIGS. 1-3, with the exception that the safety cover 106 of each subdermal needle electrodes cable assembly 100 can omitted.

The cable unit 200 includes a plurality of subdermal needle electrodes cable assemblies 201, a cable connector 205, and a safety cover 206. Lead wires 202 (i.e., signal conductors) of each one of the plurality of the subdermal needle electrodes cable assemblies 201 are adjoined to each other at a central region 210 of the cable unit 200 thereby defining a cable 203 of the cable unit 200. Such adjoining can be provided by any suitable means. Examples of such means for adjoining include, but are not limited to, electrically insulating cover being unitarily formed (e.g., a ribbon cable), the lead wires 202 being inter-wound/inter-twined, the lead wires 202 being adjoined by one or more mechanical adjoining devices, heat shrink tubing being provided over a prescribed length of adjacent portions of the lead wires 202, etc. Preferably, but not necessarily, adjoined ones of the lead wires 202 can be separated from each other adjacent the ends thereof having the needle electrode 204 attached thereto, thereby allowing the needle electrodes 204 to reach recording sites at different locations of a patient. For example, when the electrically insulating covers of the lead wires 202 are unitarily formed (e.g., a ribbon cable), the electrically insulating covers can be pulled apart such that the lead wires 202 are separated over a desired length.

Each one of the subdermal needle electrodes cable assemblies 201 includes a needle electrode 204 having a first end portion 214 and a second end portion 216. The first end portion 214 of each one of the needle electrodes 204 is configured for piercing skin of a patient and the second end portion 216 of each one of the needle electrodes 204 is electrically connected to a first end portion 218 of a respective one of the lead wires 202 by a needle electrode connector 208. In this manner, electrical continuity is provided between each needle electrode 204 and the respective lead wire 202.

The safety cover 206 is slideably (i.e., moveably) mounted on the cable 203. The cable 203 extends through a passage 222 (e.g., central passage) within the safety cover 206. The safety cover 206 is movable with respect to the cable 203 between a first position P1 in which an entire portion of each one of the needle electrodes 204 is exposed outside of the passage 222 and a second position P2 in which the entire portion of each one of the needle electrodes 204 becomes positioned within the passage 222. It is disclosed herein that, in one embodiment of the cable unit 200, the safety cover 206 is omitted and each one of the subdermal needle electrodes cable assemblies 201 includes a respective safety cover slideably mounted on the lead wire 202 thereof (e.g., a safety cover as discussed in reference to and shown in FIGS. 1-3). In this manner, the needle electrode 204 of each one of the subdermal needle electrodes cable assemblies 201 can be individually and selectively concealed with a respective safety cover.

In a similar manner as disclosed above with respect to FIGS. 1-3, the central passage 222 can include a reduced cross sectional portion for defining a maximum amount of displacement of the safety cover 206 with respect to the needle electrodes 204 when the safety cover 206 is being moved toward the first end portion 214 of the needle electrodes 204. Also in a similar manner as disclosed above with respect to FIGS. 1-3, the safety cover 206 can be configured for limiting or precluding unintentional movement toward the first position P1 once it is in the second position P2.

The cable connector 205 is connected to a second end portion 220 of each one of the lead wires 204 for allowing each one of the subdermal needle electrodes cable assemblies 201 to be electrically connected to the signal monitoring equipment in a simultaneous manner. In one embodiment, each one of the subdermal needle electrodes cable assemblies 201 includes a lead wire electrical connector (e.g., the second electrical 110 of FIGS. 1-3) having an electrically insulating cover and an electrically conductive element within the electrically insulating cover. The electrically insulating cover is fixedly mounted within a corresponding passage of the cable connector 205. The electrically conductive element is electrically connected to an electrically conductive core of the lead wire 201 and is configured for being disengagably engaged with a signal receiving terminal or port of the signal monitoring equipment. Such an embodiment allows a subdermal needle electrodes cable assembly substantially the same as the subdermal needle electrodes cable assembly 100 of FIGS. 1-3 to be used in constructing a cable unit in accordance with the present invention. Alternatively, the electrically insulating cover of the lead wire electrical connector can be omitted such that the electrically conductive element of each one of the subdermal needle electrodes cable assemblies 201 is mounted directly in a respective passage of the cable connector 205.

At least one cable retention structure 223 is attached to the cable 203. Each cable retention structure 223 includes a mounting feature 225 for allowing the cable 203 to be affixed to a support structure such as an operating table. It is disclosed herein that the cable mounting structure 223 can be attached to the cable 203 in any manner and the mounting feature 225 can be configured in any manner necessary for allowing the cable retention structure 223 to a support structure. Furthermore, it is disclosed herein that the configuration of a first cable retention structure (e.g., the mounting feature thereof) attached to the cable 203 at a first location can be different (e.g., the mounting feature thereof) than that configuration of a second cable retention structure attached to the cable 203 at a second location.

Referring now to FIG. 6, it is disclosed herein that identifying information can advantageously be provided on subdermal needle electrodes cable assemblies configured in accordance with the present invention. For example, a subdermal needle electrode cable assembly 300 can include identifying information 301 on a first electrical connector 308, a second connector 310, and/or on an identification-carrying structure 311 that is fixedly attached to a lead wire 302 thereof. The subdermal needle electrode cable assembly 100 discussed in reference to FIGS. 1-3 and the subdermal needle electrode cable assemblies 201 discussed in reference to FIGS. 4-5 are examples of the subdermal needle electrode cable assembly 300.

The identifying information 301 can include alphanumeric identifying information (e.g., A1), color-coded identifying information (e.g., A1 is a designated color), or both. When the subdermal needle electrode cable assembly 300 is part of a set of subdermal needle electrode cable assemblies, such identifying information 301 is useful in identifying the subdermal needle electrode cable assembly 300 (i.e., the needle electrode thereof) with respect to each other one of the subdermal needle electrode cable assemblies of the set. In one example, such a set of subdermal needle electrode cable assemblies is in the form of a cable unit (e.g., the cable unit 200 discussed in reference to FIGS. 4 and 5). In another example, such a set of subdermal needle electrode cable assemblies is in the form of a plurality of individual subdermal needle electrode cable assemblies (e.g., a plurality of the subdermal needle electrode cable assemblies 100 discussed in reference to FIGS. 1-3).

In the preceding detailed description, reference has been made to the accompanying drawings that form a part hereof, and in which are shown by way of illustration specific embodiments in which the present invention may be practiced. These embodiments, and certain variants thereof, have been described in sufficient detail to enable those skilled in the art to practice embodiments of the present invention. It is to be understood that other suitable embodiments may be utilized and that logical, mechanical, chemical and electrical changes may be made without departing from the spirit or scope of such inventive disclosures. To avoid unnecessary detail, the description omits certain information known to those skilled in the art. The preceding detailed description is, therefore, not intended to be limited to the specific forms set forth herein, but on the contrary, it is intended to cover such alternatives, modifications, and equivalents, as can be reasonably included within the spirit and scope of the appended claims.

What is claimed is:

1. A cable assembly, comprising:
a signal conductor;
a needle electrode electrically connected to the signal conductor; and
a safety cover having a central passage therein, wherein the signal conductor extends through the central passage and wherein the safety cover is moveable along the signal conductor for allowing the needle electrode to become positioned within the central passage.

2. The cable assembly of claim 1 wherein:
the safety cover has opposing end portions;
the central passage extends through the safety cover between said end portions;
the central passage has an electrode shrouding space at one of said end portions of the safety cover; and
the needle electrode becoming positioned within the central passage includes the needle electrode becoming positioned within the electrode shrouding space.

3. The cable assembly of claim 1 wherein:
the safety cover has a first end portion and a second end portion;
the central passage extends through the safety cover between said end portions;
the central passage has an electrode shrouding space at the first end portion of the safety cover and has a reduced cross sectional portion at the second end portion of the safety cover; and
the needle electrode becoming positioned within the central passage includes the needle electrode becoming positioned within the electrode shrouding space.

4. The cable assembly of claim 3, further comprising:
a needle electrode connector electrically connecting the needle electrode to the signal conductor;
wherein a skin piercing end portion of the needle electrode extends from a first end portion of the needle electrode connector and the signal conductor extends from a second end portion of the needle electrode connector; and
wherein the reduced cross sectional portion of the safety cover engages the needle electrode connector for defining a maximum amount of displacement of the safety cover with respect to the needle electrode when the safety cover is moved toward the skin piercing end portion of the needle electrode.

5. The cable assembly of claim 4 wherein an entire portion of the skin piercing end portion of the needle electrode is within the electrode shrouding space when the safety cover is engaged with the needle electrode connector.

6. The cable assembly of claim 1, further comprising:
a protective cover removably secured over the needle electrode for concealing a skin piercing end portion of the needle electrode prior to use of the needle electrode;
wherein the safety cover is limited from being moved along the signal conductor toward the skin piercing end portion until the protective cover is removed from its secured position over the needle electrode.

7. The cable assembly of claim 1, further comprising:
means for limiting unintentional movement of the safety cover along the signal conductor after the safety cover has been moved for allowing the needle electrode to become positioned within the central passage.

8. The cable assembly of claim 7 wherein the central passage is configured for allowing an entire portion of a skin piercing end portion of the needle electrode to become positioned within the central passage.

9. The cable assembly of claim 8 wherein:
the safety cover has a first end portion and a second end portion;
the central passage extends through the safety cover between said end portions;
the central passage has an electrode shrouding space at the first end portion of the safety cover and has a reduced cross sectional portion at the second end portion of the safety cover; and
the needle electrode becoming positioned within the central passage includes the entire portion of the skin piercing end portion of the needle electrode becoming positioned within the electrode shrouding space.

10. A cable assembly, comprising:
a lead wire;
an electrode having a first end portion and a second end portion, wherein the first end portion is configured for piercing skin of a patient and wherein the second end portion is electrically connected to the lead wire; and
a safety cover moveably mounted on the lead wire, wherein the lead wire extends through a passage within the safety cover and wherein the safety cover is movable with respect to the lead wire between a position in which the first end portion of the electrode is exposed outside of the passage and a position in which the first end portion of the electrode is positioned within the passage.

11. The cable assembly of claim 10 wherein:
the safety cover has opposing end portions;
the passage extends through the safety cover between said end portions;
the passage has an electrode shrouding space at one of said end portions of the safety cover; and
the first end portion of the electrode becoming positioned within the central passage includes an entire portion of the electrode becoming positioned within the electrode shrouding space.

12. The cable assembly of claim 10, further comprising:
an electrode connector electrically connecting the electrode to the lead wire;
wherein the first end portion of the electrode extends from a first end portion of the electrode connector and the lead wire extends from a second end portion of the electrode connector;
wherein the central passage has an electrode shrouding space at a first end portion of the safety cover and has a reduced cross sectional portion at a second end portion of the safety cover;
wherein the first end portion of the electrode becoming positioned within the central passage includes an entire portion of the electrode becoming positioned within the electrode shrouding space;
wherein the reduced cross sectional portion of the safety cover engages the electrode connector for defining a maximum amount of displacement of the safety cover with respect to the electrode when the safety cover is moved toward the first end portion of the electrode.

13. The cable assembly of claim 12, further comprising:
a protective cover removably secured over the electrode for concealing said skin piercing end portion of the electrode prior to use of the electrode;
wherein the safety cover is limited from being moved along the lead wire toward said skin piercing end portion of the electrode until the protective cover is removed from its secured position over the electrode.

14. The cable assembly of claim 10, further comprising:
means for limiting unintentional movement of the safety cover along the lead wire after the safety cover has been moved for allowing the electrode to become positioned within the central passage.

15. The cable assembly of claim 14, further comprising:
a protective cover removably secured over the electrode for concealing said skin piercing end portion of the electrode prior to use of the electrode;
wherein the safety cover is limited from being moved along the lead wire toward said skin piercing end portion of the electrode until the protective cover is removed from its secured position over the electrode;
the safety cover has opposing end portions;
the passage extends through the safety cover between said end portions;
the passage has an electrode shrouding space at one of said end portions of the safety cover; and
the first end portion of the electrode becoming positioned within the central passage includes an entire portion of the electrode becoming positioned within the electrode shrouding space.

16. A method for limiting the potential for unintentional contact with a skin piercing end portion of a needle electrode, comprising:
positioning a signal conductor of a cable assembly within a central passage of a safety cover; and
sliding the safety cover along the signal conductor toward a skin piercing end portion of a needle electrode electrically connected to an end portion of the signal conductor until the skin piercing end portion of the needle electrode becomes positioned within the central passage of the safety cover.

17. The method of claim 16, further comprising:
limiting unintentional movement of the safety cover along the signal conductor in a direction away from the skin piercing end portion of the needle electrode after the skin piercing end portion of the needle electrode becomes positioned within the central passage of the safety cover.

18. The method of claim 16 wherein:
the safety cover has a first end portion and a second end portion;
the central passage extends through the safety cover between said end portions;
the central passage has an electrode shrouding space at the first end portion of the safety cover; and
positioning the signal conductor within the central passage includes sliding the safety cover along the signal conductor until the needle electrode is entirely within the electrode shrouding space.

19. The method of claim 18 wherein:
the cable assembly includes a needle electrode connector electrically connecting the needle electrode to the signal conductor;
the central passage has a reduced cross sectional portion at the second end portion of the safety cover; and
positioning the signal conductor within the central passage includes sliding the safety cover along the signal conductor until the safety cover engages the needle electrode connector for defining a maximum amount of displacement of the safety cover with respect to the needle electrode.

20. The method of claim 19, further comprising:
limiting unintentional movement of the safety cover along the signal conductor in a direction away from the skin piercing end portion of the needle electrode after the skin piercing end portion of the needle electrode becomes positioned within the central passage of the safety cover.

* * * * *